United States Patent [19]
Fujie et al.

[11] Patent Number: 5,883,036
[45] Date of Patent: Mar. 16, 1999

[54] OLEFIN OLIGOMERIZATION CATALYST, PROCESS FOR PREPARING THE SAME, AND OLEFIN OLIGOMERIZATION PROCESS USING THE SAME

[75] Inventors: Hirokazu Fujie; Kozo Imura, both of Handa; Hideyuki Matsumoto, Machida; Takayuki Noh, Izumiohtsu; Kazuhisa Nakanishi, Yamaguchi, all of Japan

[73] Assignee: KOA Oil Company, Ltd., Japan

[21] Appl. No.: 626,628

[22] Filed: Mar. 28, 1996

[30] Foreign Application Priority Data

Mar. 29, 1995 [JP] Japan .................................. 7-071803

[51] Int. Cl.⁶ .............................. B01J 21/04; B01J 21/12; B01J 23/755; B01J 27/053
[52] U.S. Cl. .......................... 502/217; 502/222; 502/259; 502/355
[58] Field of Search .................................. 502/217, 221, 502/222, 355, 259

[56] References Cited

U.S. PATENT DOCUMENTS

| | | | |
|---|---|---|---|
| 2,794,842 | 6/1957 | Hogan et al. | 260/683.15 |
| 3,959,400 | 5/1976 | Lucki | 260/683.15 |
| 4,423,267 | 12/1983 | Dowling et al. | 585/431 |
| 4,465,788 | 8/1984 | Miller | 502/217 |
| 5,036,035 | 7/1991 | Baba et al. | 502/221 |
| 5,182,247 | 1/1993 | Kuhlmann et al. | 502/217 |

FOREIGN PATENT DOCUMENTS

| | | | |
|---|---|---|---|
| 0133052 | 2/1985 | European Pat. Off. | 37/30 |
| 0272970 | 6/1988 | European Pat. Off. | |

OTHER PUBLICATIONS

Kodansha, "Industrial Catalyst Reaction I", 1985. Catalyst Course, vol. 8., pp. 41–49 no month.

Kenichi Fukui and Chijinshokan, "Catalyst Reaction (3), Polymerization", 1977, Catalyst Industrial Course, vol. 8., pp. 3–11, 146–151. no month Japanse Publication No. 48–85506, published Nov. 13, 1973, front page.

Japanese Publication No. 49–3489, published Jan. 26, 1974, front page.

Japanese Publication No. 50–30044, published Sep. 29,1975, front page.

Japanese Publication No. 50–30046, published Sep. 29, 1975, front page.

Patent Abstracts of Japan, Publication No. 61151136 A, published Jul. 9, 1986.

Patent Abstracts of Japan, Publication No. 01225695 A, published Sep. 8, 1989.

Patent Abstracts of Japan, Publication No. 03052827 A, published Mar. 7, 1991.

Patent Abstracts of Japan, Publication No. 06287227 A, published Oct. 11, 1994.

*Primary Examiner*—Michael Lewis
*Assistant Examiner*—Alexander G. Ghyka
*Attorney, Agent, or Firm*—Webb Ziesenheim Bruening Logsdon Orkin & Hanson, P.C.

[57] ABSTRACT

An olefin oligomerization catalyst comprises at least one oxide selected from alumina and silica•alumina having a sulfate ion supported thereon. The amount of the sulfate ion contained in the catalyst is desirably in the range of 0.3 to 60% by weight based on the total weight of the alumina and/or silica•alumina and the sulfate ion. The olefin oligomerization catalyst can be readily prepared by bringing a sulfuric acid aqueous solution or an ammonium sulfate aqueous solution into contact with at least one compound selected from alumina, silica alumina and their precursors, followed by drying and calcining. Further, an olefin oligomerization catalyst comprises at least one oxide selected from alumina and silica•alumina on which a transition metal oxide is further supported in addition to the sulfate ion. By the use of the catalyst, a lower olefin produced in, for example, a petroleum refining process can be converted into an oligomer of high value added.

9 Claims, 1 Drawing Sheet

OLEFIN OLIGOMERIZATION CATALYST, PROCESS FOR PREPARING THE SAME, AND OLEFIN OLIGOMERIZATION PROCESS USING THE SAME

FIELD OF THE INVENTION

The present invention relates to an olefin oligomerization catalyst, a process for preparing the catalyst and an olefin oligomerization process using the catalyst. More particularly, the invention relates to an olefin oligomerization catalyst capable of converting a lower olefin produced by, for example, petroleum refining into an oligomer of high value added such as gasoline, kerosene or gas oil, and also relates to a process for preparing the catalyst and an olefin oligomerization process using the catalyst.

BACKGROUND OF THE INVENTION

As solid catalysts for olefin oligomerization, there are known solid acid catalysts, such as solid phosphoric acid, silica alumina and zeolite, and catalysts wherein a transition metal is supported on silica, alumina, silica•alumina or active carbon (see: "Industrial Catalyst Reaction I", Catalyst Course Vol. 8, 1985, published by Kodansha, "Catalyst Reaction (3), Polymerization", Catalyst Industrial Course Vol. 8, 1977, published by Chijinshokan).

Examples of olefin oligomerization processes using catalysts having alumina or silica alumina as a carrier include: a process using a catalyst wherein nickel sulfide is supported on a carrier of silica, alumina or silica•alumina, as described in Japanese Patent Publication No. 3489/1974; a process using a catalyst wherein nickel oxide and cobalt sulfate and/or magnesium sulfate are supported on alumina, as described in Japanese Patent Publication No. 30044/1975; a process using a nickel oxide-aluminum phosphate catalyst containing a small amount of alumina, silica or silica•alumina, as described in Japanese Patent Publication No. 30046/1975; and a process using a catalyst obtained by allowing a carrier of alumina, silica or silica•alumina to support thereon a nickel compound capable of being converted into nickel oxide by calcining and any of nitrate, sulfate and halide of a metal selected from Ca, Mg, Cd, Co, Zn, Al, Fe, Zr and Mn, or sulfate or halide of Ni, followed by calcining at 300° to 700° C., as described in Japanese Patent Laid-Open Publication No. 85506/1973.

Further, there have been proposed the following processes: an olefin oligomerization process using a catalyst wherein $Ni^{2+}$ cation is introduced into silica•alumina by means of cation exchange, as described in Japanese Patent Laid-Open Publication No. 143830/1985; and a $C_{2-6}$ olefin oligomerization process using a catalyst obtained by treating a supported composition wherein an oxide of a transition metal (M) selected from Ni, Co, Cr and Pd is supported on an acid oxide (e.g., alumina, silica•alumina, zeolite, diatomaceous earth, silica•titania and silica•magnesia), with a halogen-containing alkylaluminum compound, the atomic ratio of Al derived from the aluminum compound to the transition metal M (Al/M) being 0.5 to 10, as described in Japanese Patent Laid-Open Publication No. 151136/1986.

Furthermore, there are known other olefin oligomerization processes, such as a process in which a $C_{4-10}$ olefin-containing raw material is brought into contact with amorphous silica•alumina having an alumina content of 10 to 50% by weight, a surface area of 50 to 600 $m^2/g$ and a mean pore diameter of 10 to 100 Å under the reaction conditions of a temperature of 150° to 400° C. and a pressure of 30 to 100 $kg/cm^2$-G, as described in Japanese Patent Publication No. 434/1993; a process in which a $C_{4-10}$ olefin-containing raw material is brought into contact with a catalyst having 0.1 to 5.0% by weight of a rare earth metal supported on amorphous silica•alumina, as described in Japanese Patent Publication No. 39412/1994; and a process in which a material containing a $C_4$ olefin of normal structure as its main component is subjected to a reaction by the use of a nickel oxide support type catalyst obtained by impregnating silica•alumina, which has been preliminarily heat treated at not lower than 600° C., with a nickel salt solution to allow the silica•alumina to support 3 to 15% by weight (in terms of Ni) of nickel oxide, under the reaction conditions of a temperature of 50° to 200° C., a pressure of 20 to 100 $kg/cm^2$-G and LHSV of 0.1 to 5.0 $hr^{-1}$, to obtain a $C_8$ olefin having a degree of branching of not higher than 1.5, as described in Japanese Patent Laid-Open Publication No. 287227/1994.

These conventional catalysts, however, are not always satisfactory in oligomerization of an olefin due to their poor selectivity of dimerization and low activity. In addition, when an olefin oligomer is used, for example, as material for a phthalic acid plasticizer to be blended with polymer such as polyvinyl chloride, the olefin oligomer is desired to have a low degree of branching, i.e., few side chains. The above conventional process, however, are not always successful in obtaining a desired olefin oligomer having a sufficiently low degree of branching.

OBJECT OF THE INVENTION

The present invention has been made in the light of the prior arts as mentioned above, and it is an object of the invention to provide an olefin oligomerization catalyst which is capable of causing oligomerization of a lower olefin with prominently high activity and is excellent in selectivity of the degree of oligomerization such as dimerization, trimerization, tetramerization and pentamerization, and an olefin oligomerization catalyst which is further capable of obtaining with excellent selectivity an olefin oligomer having a low degree of branching which is useful as a material for a plasticizer. It is another object of the invention to provide a process for preparing the catalyst and an olefin oligomerization process using the catalyst.

SUMMARY OF THE INVENTION

The olefin oligomerization catalyst according to the present invention comprises at least one oxide selected from alumina and silica•alumina having a sulfate ion supported thereon.

The olefin oligomerization catalyst can be obtained by a process comprising the steps of bringing a sulfuric acid aqueous solution or an ammonium sulfate aqueous solution into contact with at least one compound selected from alumina, silica•alumina and their precursors such as alumina hydrate, aluminum hydroxide and silica•alumina gel, and calcining at a temperature at which a sulfate ion is not decomposed.

In the olefin oligomerization catalyst of the invention, a transition metal oxide or both of a transition metal oxide and aluminum oxide are further supported on the alumina and/or the silica•alumina having the sulfate ion supported thereon.

In the olefin oligomerization catalyst of the invention, it is desired that the sulfate ion is contained in an amount of 0.3 to 60% by weight, preferably 0.5 to 45% by weight in terms of $SO_4$, based on the total weight of the alumina and/or the silica•alumina and the sulfate ion.

In the olefin oligomerization catalyst wherein the transition metal oxide or both of the transition metal oxide and the aluminum oxide are further supported in addition to the sulfate ion, it is desired that the transition metal oxide is contained in an amount of 0.1 to 40% by weight in terms of a transition metal, based on the total weight of the catalyst, and the sulfate ion is contained in the aforesaid amount.

In the olefin oligomerization catalyst wherein the transition metal oxide and the aluminum oxide are further supported in addition to the sulfate ion, it is desired that the aluminum oxide is contained in an amount of 0.1 to 20% by weight in terms of aluminum, based on the total weight of the catalyst, and the sulfate ion and the transition metal oxide are contained in the aforesaid amounts.

In the present invention, the transition metal oxide is at least one compound selected from iron oxide, nickel oxide, cobalt oxide and chromium oxide, particularly preferably nickel oxide.

The process for preparing an olefin oligomerization catalyst according to the present invention comprises the steps of bringing a sulfuric acid aqueous solution or an ammonium sulfate aqueous solution into contact with at least one compound selected from alumina, silica•alumina and their precursors such as alumina hydrate, aluminum hydroxide and silica•alumina gel, and calcining at a temperature at which a sulfate ion is not decomposed, to thereby allow the alumina and/or the silica•alumina to support the sulfate ion thereon.

In the present invention, the olefin oligomerization catalyst can be also prepared by a process comprising the steps of bringing a sulfuric acid aqueous solution or an ammonium sulfate aqueous solution into contact with at least one compound selected from alumina, silica•alumina and their precursors, calcining at a temperature at which a sulfate ion is not decomposed, then bringing the alumina and/or the silica•alumina having the sulfate ion supported thereon into contact with a transition metal compound capable of being converted into an oxide by calcining or both of said transition metal compound and an aluminum compound capable of being converted into an oxide by calcining, and calcining at a temperature at which the sulfate ion is not decomposed.

In the olefin oligomerization process according to the present invention, an oligomerization raw material containing an olefin is subjected to an oligomerization reaction in the presence of the above-described olefin oligomerization catalyst.

This olefin is preferably at least an olefin of 2 to 10 carbon atoms.

As the oligomerization raw material containing an olefin, a low-boiling fraction obtained in a petroleum refining process or an ethylene plant can be employed.

In the present invention, the olefin is preferably subjected to an oligomerization reaction under the conditions of a reaction temperature of 0° to 400° C., a reaction pressure of 0 to 100 kg/cm$^2$-G and LHSV (Liquid Hourly Space Velocity) of 0.1 to 50 hr$^{-1}$.

In the invention, it is preferred that the olefin is subjected to an oligomerization reaction so as to obtain a substance selected from gasoline, kerosene and gas oil.

DETAILED DESCRIPTION OF THE INVENTION

Figure 1:
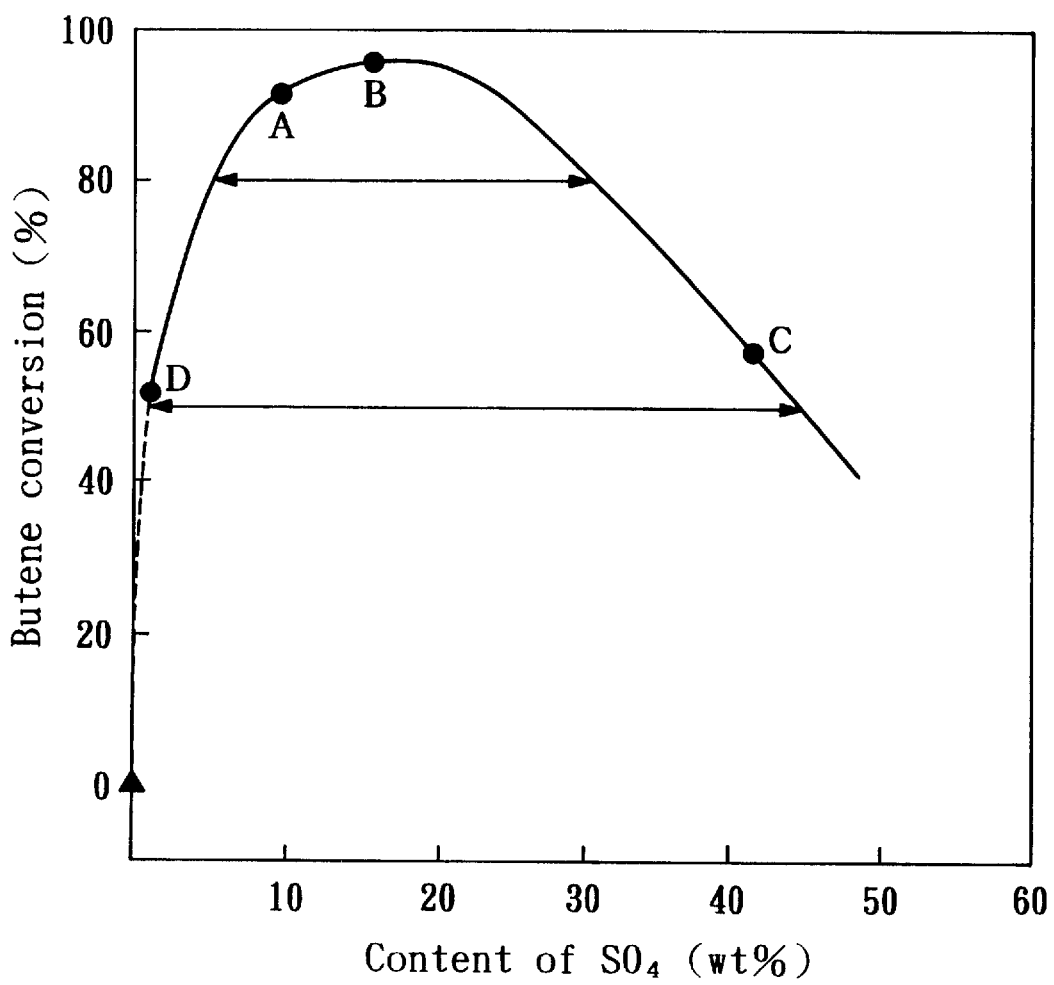
FIG. 1 is a view showing a relationship between a content of the sulfate ion in the alumina carrier and a butene conversion.

The olefin oligomerization catalyst, the process for preparing the catalyst and the olefin oligomerization process using the catalyst according to the invention will be described in detail hereinafter.

Olefin Oligomerization Catalyst

The olefin oligomerization catalyst according to the invention comprises at least one oxide selected from alumina and silica•alumina having a sulfate ion supported thereon, and the sulfate ion is desirably contained in the catalyst in an amount of 0.3 to 60% by weight, preferably 0.5 to 45% by weight, in terms of SO$_4$, based on the total weight of the alumina and/or the silica•alumina and the sulfate ion.

The olefin oligomerization catalyst can be obtained by a process comprising the steps of bringing a sulfuric acid aqueous solution or an ammonium sulfate aqueous solution into contact with at least one compound selected from alumina, silica•alumina and their precursors such as alumina hydrate, aluminum hydroxide and silica•alumina gel, and calcining at a temperature at which a sulfate ion is not decomposed.

In the olefin oligomerization catalyst of the invention, the sulfate ion is supported on the alumina and/or the silica•alumina as described above, so that an olefin can undergo oligomerization with high activity. For reference, a catalyst wherein a metal sulfate such as cobalt sulfate or magnesium sulfate is supported on alumina or silica•alumina (aforesaid JP-30044/1975 and JP-85506/1973) only exhibits low activity in the olefin oligomerization process.

Thus, the catalyst of the invention wherein the sulfate ion is supported on alumina and/or silica•alumina shows prominently high activity in the olefin oligomerization process, while the conventional catalysts wherein the metal sulfate is supported on alumina or silica•alumina shows only low activity, as is apparent from the later-described invention examples and comparative examples. That is, the action and effect of the olefin oligomerization catalyst of the invention are fundamentally different from those of the conventional catalysts due to their morphological (structural) difference. As for the olefin oligomerization catalyst of the invention, it is presumed that when the sulfate ion is supported on the alumina or the silica•alumina, the sulfate ion is generated in the form of a bidentate ligand which is linked to the Al atom present on the surface of the alumina or the silica•alumina to form an extremely strong acid site, so that the olefin oligomerization catalyst of the invention exhibits high activity, though the reason is not clear.

There is no specific limitation on the olefin oligomerization catalyst of the invention, so long as a sulfate ion per se (not a metal sulfate) is supported on the alumina and/or the silica•alumina. The alumina and/or the silica•alumina having the sulfate ion supported thereon may be used after being diluted with substances inert to the reaction or other inorganic oxides. Further, other elements may be added to the alumina and/or the silica•alumina having the sulfate ion supported thereon to use.

In the present invention, also preferred is an olefin oligomerization catalyst wherein a transition metal oxide or both of a transition metal oxide and aluminum oxide are further supported on the alumina and/or the silica•alumina having the sulfate ion supported thereon.

The transition metal oxide is at least one metal oxide selected from iron oxide, nickel oxide, cobalt oxide and chromium oxide.

Of these, nickel oxide, cobalt oxide or chromium oxide is preferred, and nickel oxide is particularly preferred.

The transition metal oxide is desirably supported in an amount of 0.1 to 40% by weight, preferably 1 to 30% by weight, in terms of a transition metal, based on the total weight of the catalyst.

The aluminum oxide is desirably supported in an amount of 0.1 to 20% by weight, preferably 0.3 to 15% by weight, in terms of aluminum, based on the total weight of the catalyst.

In the olefin oligomerization catalyst wherein the transition metal oxide or both of the transition metal oxide and the aluminum oxide are supported, it is desired that the transition metal oxide, the aluminum oxide and the sulfate ion are supported in the aforesaid amounts, respectively.

By the use of the olefin oligomerization catalyst of the invention wherein the sulfate ion is supported on the alumina and/or the silica•alumina, an olefin can undergo oligomerization with high activity as mentioned above, and oligomers of high value added, such as a dimer, a trimer, a tetramer and a pentamer of olefin, can be prepared in high yields.

The olefin oligomerization catalyst wherein the transition metal oxide is further supported on the alumina and/or the silica•alumina in addition to the sulfate ion shows high activity in the olefin oligomerization process, and an oligomer having few side chains, namely, a low degree of branching can be selectively prepared.

The olefin oligomerization catalyst wherein both of the transition metal oxide and the aluminum oxide are further supported in addition to the sulfate ion is much more improved in the selectivity of the low degree of branching, and particularly, an oligomerization reaction at a high temperature can be carried out with excellent selectivity of the low degree of branching.

The term "degree of branching" as used herein means a number of the chain hydrocarbon groups (methyl, ethyl) branched from the main hydrocarbon chain of the α-olefin structure. For example, in the case of an olefin of 8 carbon atoms (i.e., dimer of butene), normal octene has a degree of branching of 0, methylheptene has that of 1, dimethylhexene has that of 2, and trimethylpentene has that of 3. The term "average degree of branching" as used herein means an average value of the degrees of branching of the mixed olefins.

Process for Preparing Olefin Oligomerization Catalyst

In the present invention, there is no specific limitation on the process for preparing the olefin oligomerization catalyst comprising alumina and/or silica•alumina having a sulfate ion supported thereon, so long as the sulfate ion per se can be supported on the alumina and/or the silica•alumina.

However, it is preferred that the olefin oligomerization catalyst is prepared by a process comprising the steps of bringing a sulfuric acid aqueous solution or an ammonium sulfate aqueous solution into contact with at least one compound selected from alumina, silica•alumina and their precursors such as alumina hydrate, aluminum hydroxide and silica•alumina gel, and calcining at a temperature at which the sulfate ion is not decomposed, as described before. In more detail, the catalyst of the present invention can be prepared by a process comprising the steps of treating the alumina and/or the silica•alumina with a sulfuric acid aqueous solution or an ammonium sulfate aqueous solution by means of impregnation, immersion, kneading or the like so as to allow the alumina and/or the silica•alumina to support the sulfate ion, followed by drying and calcining.

The calcining temperature is in the range of 300° to 800° C., preferably 400° to 700° C. As the alumina or the silica•alumina, commercially available ones are employable. Aluminum hydrate, aluminum hydroxide or a silica•alumina gel is also employable by treating it with the sulfuric acid aqueous solution or the ammonium sulfate aqueous solution.

The catalyst wherein the transition metal oxide is further supported can be prepared by bringing the alumina and/or the silica•alumina, on which the sulfate ion is preliminarily supported, into contact with a transition metal oxide-forming material, i.e., a compound capable of being converted into a transition metal oxide by calcining or decomposition in an inert gas such as nitrogen or in air. Examples of the transition metal oxide-forming materials include inorganic salts such as nitrates, carbonates and halides of transition metals, organic salts such as oxalates and acetates of transition metals, and ammonia complex salts. Examples of the aluminum oxide-forming materials include aluminum nitrate, aluminum sulfate and aluminum halides.

For allowing the alumina and/or silica•alumina having the sulfate ion supported thereon to support the transition metal oxide or both of the transition metal oxide and the aluminum oxide, the alumina and/or silica•alumina containing the sulfate ion is treated with the metallic salt aqueous solution or ammonia complex salt aqueous solution serving as the transition metal oxide-forming material and the metallic salt aqueous solution serving as the aluminum oxide-forming material by a method conventionally used for the catalyst preparation, such as impregnation, immersion, co-deposition, deposition or kneading, and then the thus treated product is dried and calcined (decomposed). In this method, the calcining temperature is a temperature at which the transition metal oxide-forming material is decomposed in an inert gas or air to produce a transition metal oxide, and it is in the range of usually 300° to 800° C., preferably 400° to 700° C. The transition metal oxide and the aluminum oxide may be simultaneously supported on the alumina and/or silica•alumina having the sulfate ion supported thereon, or the aluminum oxide may be supported before or after the transition metal oxide is supported. However, the simultaneous supporting is economically advantageous. The morphology of the aluminum oxide thus supported on the alumina and/or silica•alumina having the sulfate ion supported thereon is not clear, but it is presumed that the aluminum oxide serves to stabilize oxidation state of the transition metal. The catalyst wherein the transition metal oxide and the aluminum oxide are further supported on the alumina and/or the silica•alumina in addition to the sulfate ion may be used after being diluted with substances inert to the reaction or other inorganic oxides, or other ingredients may be added to the catalyst to use.

It is preferred that the catalyst wherein the sulfate ion is supported on the alumina and/or the silica•alumina and the catalyst wherein the transition metal oxide and the aluminum oxide are further supported on the alumina and/or the silica•alumina in addition to the sulfate ion are dried under heating in an inert gas before they are used for the olefin oligomerization reaction. The catalyst is appropriately used in the form of a powder or a molded product in accordance with the reaction type.

Olefin Oligomerization Process

In the olefin oligomerization process according to the invention, an oligomerization raw material containing an olefin is subjected to an oligomerization reaction in the presence of the olefin oligomerization catalyst described above.

The olefin is preferably at least an olefin of 2 to 10 carbon atoms.

In the present invention, one kind of an olefin may be subjected to an oligomerization reaction or two or more kinds of olefins may be subjected to the reaction.

The olefin used herein is, for example, a low-boiling fraction obtained in a petroleum refining process or an ethylene plant. Specifically, an olefin fraction produced in a FCC apparatus or an olefin fraction produced in an ethylene cracker or a coker can be employed. These fractions may be used in combination.

In the present invention, only an olefin may be used as the oligomerization raw material containing an olefin, but it is preferred that the olefin is diluted with an inert substance such as saturated hydrocarbon, because the temperature rise caused by heat of reaction can be suppressed.

The olefin oligomerization of the invention may be carried out in accordance with any reaction systems such as a batchwise system, fixed bed system and fluidized bed system.

The reaction temperature varies depending on the reactivity of the olefin, but it is in the range of usually 0° to 400° C., preferably 0° to 300° C.

According to the invention, a higher olefin conversion can be realized at a relatively low temperature as compared with the case of using the conventional catalysts. The reaction can be carried out at atmospheric pressure or under pressure by any of a liquid phase process and a gas phase process. For example, when an olefin of 3 to 4 carbon atoms is mainly used, it is preferred that the reaction temperature is in the range of 0° to 300° C. and the reaction pressure is in the range of 5 to 100 kg/cm$^2$-G. The contact time is in the range of 0.1 to 50 hr$^{-1}$, preferably 0.1 to 15 hr$^{-1}$, in terms of LHSV.

In the invention, by conducting oligomerization of an olefin, an oligomer of high value added, such as gasoline, kerosene or gas oil, can be obtained in a high yield.

Further, in the invention, an olefin oligomer having a low degree of branching which is useful as a material of a plasticizer, can be obtained with excellent selectivity of the low degree of branching.

According to the catalyst of the invention, alumina or silica•alumina which is a stable and inexpensive solid acid is used as a carrier, so that the production cost is low. Further, the sulfate ion supported on the alumina or the silica•alumina is stably present, so that a problem of apparatus corrosion or separation does not take place. Moreover, when the catalyst is used in an olefin oligomerization process, the equipment cost and the operation cost can be decreased, and an oligomer of high value added can be selectively obtained in a high yield due to the catalyst having prominently high activity. By the use of the catalyst wherein a transition metal oxide such as nickel oxide is further supported on the alumina or the silica•alumina in addition to the sulfate ion, an olefin having a low degree of branching can be selectively obtained in a high yield.

EXAMPLE

The present invention will be further described with reference to the following examples, but it should be construed that the invention is in no way limited to those examples.

Catalyst Preparation Example 1

A sulfuric acid (special grade chemical, >96%, available from Wako Pure Chemical Industries, Ltd.) was diluted with distilled water to give a sulfuric acid aqueous solution having a concentration of 14.6 g/100 ml. Then, a commercially available alumina carrier (DC-2282, γ-Al$_2$O$_3$, available from Mitsubishi Chemical Industries, Ltd.) was impregnated with 66 ml of the sulfuric acid aqueous solution per 100 g of the carrier. The quantity of the impregnation solution corresponded to a water absorption of the alumina carrier. After the impregnation, the thus treated alumina carrier was dried at 110° C. overnight and calcined at 500° C. for 3 hours in an air stream, to obtain an alumina catalyst A wherein a sulfate ion was supported. The content of the sulfate ion in the catalyst measured by Leco method (using a Sulfur Analyzer SC-132 produced by Leco Corporation) was 3.1% by weight in terms of S and 9.3% by weight in terms of SO$_4$. Then, the above procedure was repeated except that the concentration of the sulfuric acid aqueous solution was varied, to prepare catalyst B (sulfate ion content: 15.3% by weight in terms of SO$_4$), catalyst C (sulfate ion content: 41.7% by weight in terms of SO$_4$) and catalyst D (sulfate ion content: 0.6% by weight in terms of SO$_4$).

Examples 1–4, Comparative Example 1

A fixed bed flow type reactor having an inner diameter of 16 mm was charged with 60 ml of catalyst A. To the reactor, a C$_4$ olefin-containing material having a composition shown in Table 1 was fed, to perform oligomerization reaction under the conditions of a reaction pressure of 50 kg/cm$^2$-G, LHSV of 1.0 hr$^{-1}$ and a temperature shown in Table 2. Similarly, an oligomerization reaction was carried out by the use of catalyst B, catalyst C, catalyst D or untreated alumina containing no sulfate ion under the temperature conditions shown in Table 2. The results obtained after 24 hours from the initiation of the reaction are set forth in Table 2 and FIG. 1.

TABLE 1

| | |
|---|---|
| Propane | 0.5% by weight |
| i-Butane | 40.0% by weight |
| n-Butane | 12.0% by weight |
| i-Butene | 3.0% by weight |
| 1-Butene | 7.0% by weight |
| 2-Butene | 37.5% by weight |

TABLE 2

| | Example | | | | Comp. Example |
|---|---|---|---|---|---|
| | 1 | 2 | 3 | 4 | 1 |
| Catalyst | A | B | C | D | |
| Carrier | Alumina | Alumina | Alumina | Alumina | Alumina |
| Content of SO$_4$ (wt %) | 9.3 | 15.3 | 41.7 | 0.6 | — |
| Reaction Temperature (°C.) | 100 | 17 50 100 150 | 100 | 100 | 100 |

TABLE 2-continued

|  | Example | | | | | Comp. Example |
|---|---|---|---|---|---|---|
|  | 1 | 2 | | 3 | 4 | 1 |
| Butene conversion (%) | 93 | 58 | 79 | 97 | 100 | 57 | 53 | 0 |
| Selectivity of dimer (%) | 37 | 79 | 69 | 30 | 20 | 75 | 77 | — |
| Selectivity of trimer and tetramer (%) | 53 | 20 | 30 | 60 | 64 | 23 | 21 | — |
| Yield of dimer (%) | 34 | 46 | 55 | 29 | 20 | 43 | 41 | — |
| Yield of trimer and tetramer (%) | 49 | 16 | 24 | 58 | 64 | 13 | 11 | — |

FIG. 1 graphically shows the test results obtained at 100° C. among those shown in Table 2. In this figure, the content of the sulfate ion in the catalyst [weight of sulfate ion÷(weight of alumina+weight of sulfate ion)×100(%)] is plotted as ordinate and the butene conversion is plotted as abscissa. As is evident from Table 2 and FIG. 1, by introducing only 0.6% of the sulfate ion (Example 4), the butene conversion abruptly increased up to 53% from 0% as compared with the alumina containing no sulfate ion (Comparative Example 1: symbol ▲ in FIG. 1). Further, the butene conversion became not less than 50% when the content of the sulfate ion was in the range of 0.5 to 45% by weight, and it became not less than 80% when the sulfate ion content was in the range of 5 to 30% by weight.

Even after the reaction was continued for about 400 hours at a reaction temperature of 150° C. (Example 2), no decrease of activity was observed and the content of the sulfate ion in the catalyst was the same as before the reaction. According to the invention, as is evident from Table 2, the butene conversion is high even at a low temperature and an oligomer can be selectively obtained in a high yield. Further, a dimer, i.e., gasoline fraction, and a trimer or a tetramer, i.e., kerosene fraction or gas oil fraction, can be selectively obtained in high yields by controlling the reaction temperature. Moreover, there is no problem of apparatus corrosion because the sulfate ion supported is stably present.

Catalyst Preparation Example 2

An iron oxide carrier (N-IDS, available from Nissan Girdler Co. Ltd.), a zinc oxide carrier (N-748, available from Nikki Chemical Co., Ltd.), a silica carrier (N-602, available from Nikki Chemical Co., Ltd.) and a silica alumina carrier (IS-28, available from Catalysts & Chemicals Industries Co., Ltd.) were each impregnated with a sulfuric acid aqueous solution having a concentration of 15% by weight in terms of $SO_4$, then dried and calcined in a manner similar to that of Catalyst Preparation Example 1, to obtain catalyst E, catalyst F, catalyst G and catalyst H each having a sulfate ion content shown in Table 3.

Example 5, Comparative Examples 2–5

An oligomerization reaction was carried out in a manner similar to that of Example 1 by the use of catalyst E (Comparative Example 2), catalyst F (Comparative Example 3), catalyst G (Comparative Example 4), catalyst H (Example 5) or untreated silica alumina containing no sulfate ion (Comparative Example 5) under the temperature conditions shown in Table 3. The results obtained after 24 hours from the initiation of the reaction are set forth in Table 3.

TABLE 3

|  | Comparative Example | | | Example | Comp. Exam. |
|---|---|---|---|---|---|
|  | 2 | 3 | 4 | 5 | 5 |
| Catalyst | E | F | G | H | |
| Carrier | Iron oxide | Zinc oxide | Silica | Silica alumina | Silica alumina |
| Content of $SO_4$ (wt %) | 16.2 | 8.1 | 2.1 | 15.3 | — |
| Reaction Temperature (°C.) | 100 | 100 | 100 | 50  100 | 100 |
| Butene conversion (%) | 15 | 7 | 0 | 50  89 | 36 |
| Selectivity of dimer (%) | 78 | 91 | — | 76  39 | 91 |
| Selectivity of trimer and tetramer (%) | 22 | 9 | — | 22  54 | 7 |
| Yield of dimer (%) | 12 | 6 | — | 38  35 | 33 |
| Yield of trimer and tetramer (%) | 3 | 1 | — | 11  48 | 3 |

As is evident from Table 3, the butene conversion was low even when the catalyst wherein the sulfate ion was supported on iron oxide, zinc oxide or silica was used. However, by the use of the catalyst wherein the sulfate ion was supported on the silica alumina, the butene conversion and the yield of trimer and tetramer were obviously improved. Further, the silica•alumina having the sulfate ion supported thereon showed high activity even at a low temperature.

Examples 6 and 7, Comparative Example 6

An oligomerization reaction was carried out in a manner similar to that of Example 1 using catalyst B and catalyst H and using a $C_8$ olefin-containing material having a composition shown in Table 4 under the conditions of a reaction pressure of 70 kg/cm$^2$-G, LHSV of 2.0 hr$^{-1}$. The results obtained after 24 hours from the initiation of the reaction are set forth in Table 5 in which the results obtained by the use of the silica•alumina containing no sulfate ion (Comparative Example 6) are also set forth. By introducing the sulfate ion, a high octene conversion and a high yield of trimer and tetramer were obtained at a relatively low temperature.

TABLE 4

| i-Octane | 70.0% by weight |
|---|---|
| 1-Octene | 30.0% by weight |

TABLE 5

|  | Example | | Comparative Example |
|---|---|---|---|
|  | 6 | 7 | 6 |
| Catalyst | B | H |  |
| Carrier | Alumina | Silica alumina | Silica alumina |
| Content of SO$_4$ (wt %) | 15.3 | 15.3 | — |
| Reaction Temperature (°C.) | 150 | 180 | 200 |
| 1-octene conversion (%) | 70 | 53 | 41 |
| Selectivity of dimer (%) | 63 | 72 | 65 |
| Selectivity of trimer (%) | 27 | 16 | 25 |
| Yield of dimer and trimer (%) | 63 | 47 | 37 |

Catalyst Preparation Example 3

A sulfuric acid (special grade chemical, >96%, available from Wako Pure Chemical Industries, Ltd.) was diluted with distilled water to give a sulfuric acid aqueous solution having a concentration of 11.2 g/100 ml. Then, a commercially available alumina carrier (DC-2282, γ-Al$_2$O$_3$, available from Mitsubishi Chemical Corporation) was impregnated with 66 ml of the sulfuric acid aqueous solution per 100 g of the carrier. The quantity of the impregnation solution corresponded to a water absorption of the alumina carrier. After the impregnation, the thus treated alumina carrier was dried at 110° C. overnight and calcined at 500° C. for 3 hours in an air stream, to obtain a sulfate ion-containing alumina carrier (sulfate ion content: 6.9% by weight in terms of SO$_4$). The sulfate ion-containing alumina carrier was further impregnated with a nickel nitrate aqueous solution, then dried and calcined at 500° C. for 3 hours in an air stream, to prepare catalyst I wherein NiO was supported in an amount of 10% by weight in terms of Ni, based on the total weight of the catalyst (weight of sulfate ion-containing alumina+weight of nickel oxide) (sulfate ion content based on total weight of catalyst after supporting of nickel oxide: 6.0% by weight in terms of SO$_4$). Similarly, catalyst J wherein nickel oxide was further supported after supporting of the sulfate ion on a silica•alumina carrier (IS-28, available from Catalysts & Chemicals Industries Co., Ltd.), catalyst K wherein nickel oxide was supported on untreated alumina containing no sulfate ion (DC-2282, available from Mitsubishi Chemical Corporation) and catalyst L wherein nickel oxide was supported on untreated silica•alumina containing no sulfate ion were prepared.

Examples 8 and 9, Comparative Examples 7 and 8

A fixed bed flow type reactor having an inner diameter of 16 mm was charged with 10 ml of catalyst I, J, K or L. To the reactor, ethylene was fed at a feed rate of 3,000 ml/hr to perform oligomerization reaction at a reaction temperature of 200° C. and at atmosphere. The results obtained after 5 hours from the initiation of the reaction are set forth in Table 6.

TABLE 6

|  | Example | | Comparative example | |
|---|---|---|---|---|
|  | 8 | 9 | 7 | 8 |
| Catalyst | I | J | K | L |
| Carrier | Alumina | Silica alumina | Alumina | Silica alumina |
| Content of SO$_4$ (%) *1 | 6.9 | 6.9 | — | — |
| Content of SO$_4$ based on total amount of catalyst (%) *2 | 6.0 | 6.0 | — | — |
| Amount of Ni supported (%) | 10 | 10 | 10 | 10 |
| Reaction temperature (°C.) | 200 | 200 | 200 | 200 |
| Ethylene conversion (%) | 53 | 38 | 0.5 | 3 |
| Selectivity of n-butene (%) | 86 | 85 |  |  |

Remarks
*1: weight of sulfate ion ÷ (weight of carrier + weight of sulfate ion) × 100 (%)
*2: weight of sulfate ion ÷ (weight of carrier + weight of sulfate ion + weight of nickel oxide) × 100 (%)

As is evident from Table 6, the catalysts I and J wherein nickel oxide was supported on the sulfate ion-containing alumina and the sulfate ion-containing silica•alumina, respectively, were superior in both the ethylene conversion and the selectivity of n-butene to catalysts K and L wherein the nickel oxide was supported on the alumina containing no sulfate ion and the silica•alumina containing no sulfate ion, respectively.

Examples 10 and 11, Comparative Examples 9 and 10

A fixed bed flow type reactor having an inner diameter of 16 mm was charged with 60 ml of each catalyst having a composition shown in Table 7. To the reactor, a propane-propylene mixed material containing 79.7% by weight of propylene was fed to perform oligomerization reaction under the conditions of a reaction pressure of 60 kg/cm$^2$-G and LHSV of 1.0 hr$^{-1}$. The results obtained after 24 hours from the initiation of the reaction are set forth in Table 7.

TABLE 7

|  | Example | | Comparative example | |
|---|---|---|---|---|
|  | 10 | 11 | 9 | 10 |
| Catalyst | I | J | K | L |
| Carrier | Alumina | Silica alumina | Alumina | Silica alumina |
| Content of SO$_4$ (%) *1 | 6.9 | 6.9 | — | — |
| Content of SO$_4$ based on total amount of catalyst (%) *2 | 6.0 | 6.0 | — | — |
| Amount of Ni supported (%) | 10 | 10 | 10 | 10 |
| Reaction temperature (°C.) | 50 | 100 | 50 | 100 |
| Propylene conversion (%) | 83 | 62 | 0.6 | 45 |
| Selectivity of C$_6$ olefin (%) | 76 | 73 |  | 19 |
| Selectivity of C$_9$ olefin (%) | 17 | 14 |  | 36 |
| Average degree of branching of C$_6$ olefin | 0.61 | 0.86 |  | 1.44 |

*1 and *2: See remarks of Table 6.

As is evident from Table 7, catalysts I and J wherein nickel oxide was supported on the sulfate ion-containing alumina and the sulfate ion-containing silica•alumina, respectively, were superior in both the propylene conversion and the selectivity of C$_6$ olefin to catalysts K and L wherein the nickel oxide was supported on the alumina containing no sulfate ion or the silica•alumina containing no sulfate ion, respectively. Further, a $C_6$ olefin having a low degree of branching was obtained by the use of catalyst I or J.

Catalyst Preparation Example 4

The alumina carrier containing 6.9% by weight of the sulfate ion, which was obtained in Catalyst Preparation Example 3, was impregnated with a nickel nitrate aqueous solution in the same manner as in Catalyst Preparation Example 3 except for varying the concentration of the nickel nitrate aqueous solution, then dried and calcined, to obtain catalysts M and N wherein nickel oxide was supported. Separately, the alumina carrier containing 6.9% by weight of the sulfate ion was pulverized into grains of 100 mesh and under and then introduced into a nickel nitrate aqueous solution having a concentration of 1 mol/l. To the resulting mixture was dropwise added an ammonium carbonate aqueous solution having a concentration of 1 mol/l with stirring at 35° C., to adjust pH of the mixture to 7. The mixture was then filtered, dried and calcined at 500° C. for 3 hr, to prepare catalyst O wherein NiO was supported in an amount of 25% by weight in terms of Ni. Further, the alumina carrier containing 6.9% by weight of the sulfate ion was impregnated with a mixture of a nickel nitrate aqueous solution and an aluminum nitrate aqueous solution, then dried and calcined at 500° C. for 3 hours in air, to prepare a catalyst P wherein NiO was supported in an amount of 8% by weight in terms of Ni and aluminum oxide was supported in an amount of 3% by weight in terms of Al.

Examples 12–17, Comparative Examples 11 and 12

A fixed bed flow type reactor was charged with 60 ml of catalyst I, M, N, O, P, L or K in a manner similar to that of Example 10. To the reactor, a $C_4$ fraction material containing a $C_4$ olefin of a composition shown in Table 8 was fed, to perform butene oligomerization reaction under the conditions of a reaction pressure of 50 kg/cm$^2$-G and LHSV of 1.0 hr$^{-1}$. The results obtained after 24 hours from the initiation of the reaction are set forth in Tables 9 and 10.

TABLE 8

| i-Butane | 40.0% by weight |
|---|---|
| n-Butane | 12.0% by weight |
| i-Butene | 0.5% by weight |
| 1-Butene | 7.0% by weight |
| 2-Butene | 40.5% by weight |

TABLE 9

| | Example | | | |
|---|---|---|---|---|
| | 12 | 13 | 14 | 15 |
| Catalyst | I | M | N | O |
| Carrier | Alumina | Alumina | Alumina | Alumina |
| Content of SO$_4$ (%) *1 | 6.9 | 6.9 | 6.9 | 6.9 |
| Content of SO$_4$ based on total amount of catalyst (%) *2 | 6.0 | 6.5 | 6.9 | 3.2 |
| Amount of Ni supported (%) | 10 | 5 | 1.0 | 25 |
| Reaction temperature (°C.) | 50 100 150 | 50 | 50 | 100 |
| Butene conversion (%) | 75 72 65 | 72 | 74 | 58 |
| Selectivity of C$_8$ olefin (%) | 82 79 80 | 81 | 78 | 78 |
| Average degree of branching of C$_8$ olefin | 1.14 1.04 1.11 | 1.18 | 1.48 | 1.14 |

*1 and *2: See remarks of Table 6.

TABLE 10

| | Example | | Comp. Example | |
|---|---|---|---|---|
| | 16 | 17 | 11 | 12 |
| Catalyst | P | J | K | L |
| Carrier | Alumina | Silica alumina | Alumina | Silica alumina |
| Content of SO$_4$ (%) *1 | 6.9 | 6.9 | — | — |
| Content of SO$_4$ based on total amount of catalyst (%) *2 | 5.4 | 6.0 | — | — |
| Amount of Ni supported (%) | 8 | 10 | 10 | 10 |
| Amount of Al supported (%) | 3 | — | — | — |
| Reaction temperature (°C.) | 100 150 175 | 100 | 100 | 100 |
| Butene conversion (%) | 71 64 61 | 75 | 1 | 61 |
| Selectivity of C$_8$ olefin (%) | 80 81 79 | 80 | | 70 |

TABLE 10-continued

|  | Example | | Comp. Example | |
|---|---|---|---|---|
|  | 16 | 17 | 11 | 12 |
| Average degree of branching of $C_8$ olefin | 1.04 | 1.04 | 1.19 | 1.17 | 1.71 |

*1: See remarks of Table 6.
*2: weight of sulfate ion ÷ (weight of carrier + weight of sulfate ion + weight of nickel oxide + weight of aluminium oxide) × 100 (%)

The catalyst of the invention wherein nickel oxide was supported on the sulfate ion-containing alumina or silica•alumina carrier had a higher butene conversion as compared with the catalyst which was alumina or silica•alumina containing no sulfate ion, and a $C_8$ olefin having a low degree of branching was selectively obtained. Further, the catalyst of the invention showed a high butene conversion even at a low temperature, and a $C_8$ olefin having a low degree of branching was selectively obtained. Furthermore, it was confirmed that the degree of branching of the $C_8$ olefin was decreased particularly in the oligomerization reaction at a high temperature by the use of the catalyst obtained by allowing the sulfate ion-containing carrier to further support aluminum oxide in addition to the nickel oxide.

Example 18

An alumina hydrate was prepared by neutralization reaction of a sodium aluminate and aluminum sulfate in accordance with a method described in "Catalyst Preparation Chemistry" p. 207, by Ozaki, et al., published by Kodansha, 1980. To the amorphous and pseudo-boehmite alumina hydrate powder obtained by drying the alumina hydrate at 110° C. was dropwise added a sulfuric acid aqueous solution. Then, the mixture was kneaded, then adjusted in its water content and extrusion molded. The molded product was dried at 110° C. overnight by means of a dryer and calcined at 550° C. for 3 hours in an air stream, to obtain a sulfate ion-containing γ-alumina carrier. The content of the sulfate ion in the alumina was 8.4% by weight in terms of $SO_4$. The sulfate ion-containing alumina carrier was impregnated with a nickel nitrate aqueous solution in a manner similar to that in the preparation of catalyst I, then dried at 110° C. and calcined at 500° C. for 3 hours in an air stream, to obtain a catalyst wherein NiO was supported in an amount of 10% by weight in terms of Ni (sulfate ion content based on total weight of catalyst after supporting of nickel oxide: 7.2% by weight in terms of $SO_4$). Then, a butene oligomerization reaction was carried out under the same conditions as in Examples 12–17. The results are set forth in Table 11.

TABLE 11

| Reaction temperature | 50° C. |
|---|---|
| Butene conversion | 74% |
| Selectivity of $C_8$ olefin | 82% |
| Average degree of branching of $C_8$ olefin | 1.15 |

Comparative Example 13

An alumina carrier was impregnated with a mixture of a nickel nitrate aqueous solution and a cobalt sulfate aqueous solution, then calcined at 500° C. for 3 hours in an air stream and allowed to stand at the same temperature for 2 hours in an nitrogen stream, to obtain a catalyst. The content of NiO in the catalyst was 1.6% by weight in terms of Ni, and the content of $COSO_4$ in the catalyst was 9.5% by weight. Using a material containing a $C_4$ olefin of a composition shown in Table 8, an oligomerization reaction was carried out under the same conditions as in Example 12. The results are set forth in Table 12. The thus obtained catalyst having the metal sulfate of the sulfate group supported on the carrier (conventional catalyst wherein cobalt sulfate was supported on alumina carrier, prepared by methods of Japanese Patent Publication No. 30044/1975 and Japanese Patent Laid-Open Publication No. 85506/1973) had an extremely lower butene conversion, as compared with the catalysts of the invention wherein the sulfate ion per se (not the metal sulfate) was supported on alumina (Examples 12 to 16 in Tables 9 and 10). Further, the average degree of branching of the resulting $C_8$ olefin was very high.

TABLE 12

| Reaction temperature | 50° C. |
|---|---|
| Butene conversion | 14% |
| Selectivity of $C_8$ Olefin | 93% |
| Average degree of branching of $C_8$ olefin | 1.98 |

What is claimed is:

1. An olefin oligomerization catalyst comprising at least one oxide selected from the group consisting of alumina and silica•alumina, said oxide having a sulfate ion per se and nickel oxide wherein said catalyst is obtained by a process comprising the steps of:

(A) bringing a sulfuric acid aqueous solution or an ammonium sulfate aqueous solution into contact with at least one non-nickelous compound selected from the group consisting of alumina and silica•alumina;

(B) calcining at a temperature at which a sulfate ion is not decomposed;

(C) bringing the calcined product into contact with a nickel compound capable of being converted into nickel oxide by calcining; and (D) calcining at a temperature at which a sulfate ion is not decomposed, wherein the sulfate ion is contained in an amount of 0.3 to 60% by weight in terms of $SO_4$, based on the total weight of the alumina and/or the silica•alumina and the sulfate ion.

2. The olefin oligomerization catalyst as claimed in claim 1, wherein the nickel oxide is contained in an amount of 0.1 to 40% by weight in terms of nickel, based on the total weight of the catalyst.

3. A process for preparing an olefin oligomerization catalyst comprising the steps of:

(A) bringing a sulfuric acid aqueous solution or an ammonium sulfate aqueous solution into contact with at least one non-nickelous compound selected from the group consisting of alumina and silica•alumina;

(B) calcining at a temperature at which a sulfate ion is not decomposed;

(C) bringing the calcined product into contact with a nickel compound capable of being converted into nickel oxide by calcining; and (D) calcining at a temperature at which a sulfate ion is not decomposed.

4. The olefin oligomerization catalyst as claimed in claim 1, wherein said catalyst is obtained by a process consisting of the steps (A), (B), (C) and (D) in this order.

5. The olefin oligomerization catalyst as claimed in claim 1, wherein the calcining temperature in the steps (B) and (D) is in the range of 300° to 800° C.

6. The olefin oligomerization catalyst as claimed in claim 5, wherein the calcining temperature in the steps (B) and (D) is in the range of 400° to 700° C.

7. The process for preparing an olefin oligomerization catalyst as claimed in claim 3, wherein the process consists of the steps (A), (B), (C) and (D) in this order.

8. The process for preparing an olefin oligomerization catalyst as claimed in claim 3, wherein the calcining temperature in the steps (B) and (D) is in the range of 300° to 800° C.

9. The process for preparing an olefin oligomerization catalyst as claimed in claim 8, wherein the calcining temperature in the steps (B) and (D) is in the range of 400° to 700° C.

* * * * *

UNITED STATES PATENT AND TRADEMARK OFFICE
CERTIFICATE OF CORRECTION

PATENT NO. : 5,883,036
DATED : March 16, 1999
INVENTOR(S) : Hirokazu Fujie et al.

It is certified that error appears in the above-identified patent and that said Letters Patent is hereby corrected as shown below:

Column 7 Line 15 "systems" should read --system--.

Column 15 Table 10, first column, last item in row: after "olefin" insert --(%)--.

Signed and Sealed this

Seventh Day of September, 1999

Attest:

Q. TODD DICKINSON

Attesting Officer     Acting Commissioner of Patents and Trademarks